United States Patent

Castor

Patent Number: 6,014,889
Date of Patent: Jan. 18, 2000

[54] GAS ANALYZER

[75] Inventor: Rolf Castor, Hagersten, Sweden

[73] Assignee: Siemens Elema AB, Solna, Sweden

[21] Appl. No.: 09/184,060

[22] Filed: Nov. 2, 1998

[30] Foreign Application Priority Data

Nov. 25, 1997 [SE] Sweden .................................. 9704329

[51] Int. Cl.[7] .......................... G01N 29/02; G01N 33/00; G01J 1/42
[52] U.S. Cl. .......................... 73/24.01; 436/136; 250/343
[58] Field of Search ............................ 73/24.01, 24.02; 436/136; 250/343

[56] References Cited

U.S. PATENT DOCUMENTS

| | | | |
|---|---|---|---|
| 5,141,331 | 8/1992 | Oehler et al. | 73/24.01 |
| 5,143,695 | 9/1992 | van den Burg | 422/84 |
| 5,285,677 | 2/1994 | Oehler . | |
| 5,692,497 | 12/1997 | Schnitzer et al. | 128/204.21 |
| 5,753,797 | 5/1998 | Forster et al. | 73/24.01 |
| 5,792,665 | 8/1998 | Morrow, III | 436/136 |

*Primary Examiner*—Hezron Williams
*Assistant Examiner*—Jay L. Politzer
*Attorney, Agent, or Firm*—Hill & Simpson

[57] ABSTRACT

A gas analyzer has a test chamber for a gas sample, an inlet for the gas sample and a gas sensor sensitive to gas movement, for determining the concentration of a constituent gas in the gas sample. The inlet is adapted to be connected to an inspiration line of a respirator. A shield is arranged so it covers the inlet of the test chamber, causing the gas sample to remain relatively still inside the test chamber during the analysis, regardless of the main flow of the gas to be analyzed. The gas analyzer can accordingly be devised for direct connection to the gas to be analyzed.

10 Claims, 1 Drawing Sheet

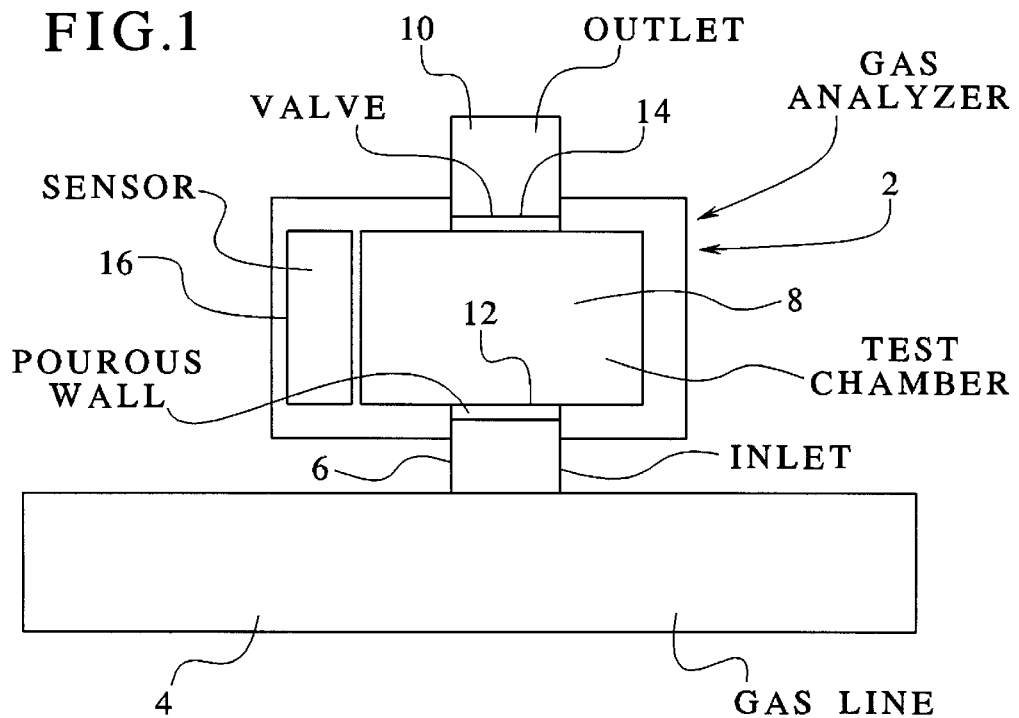
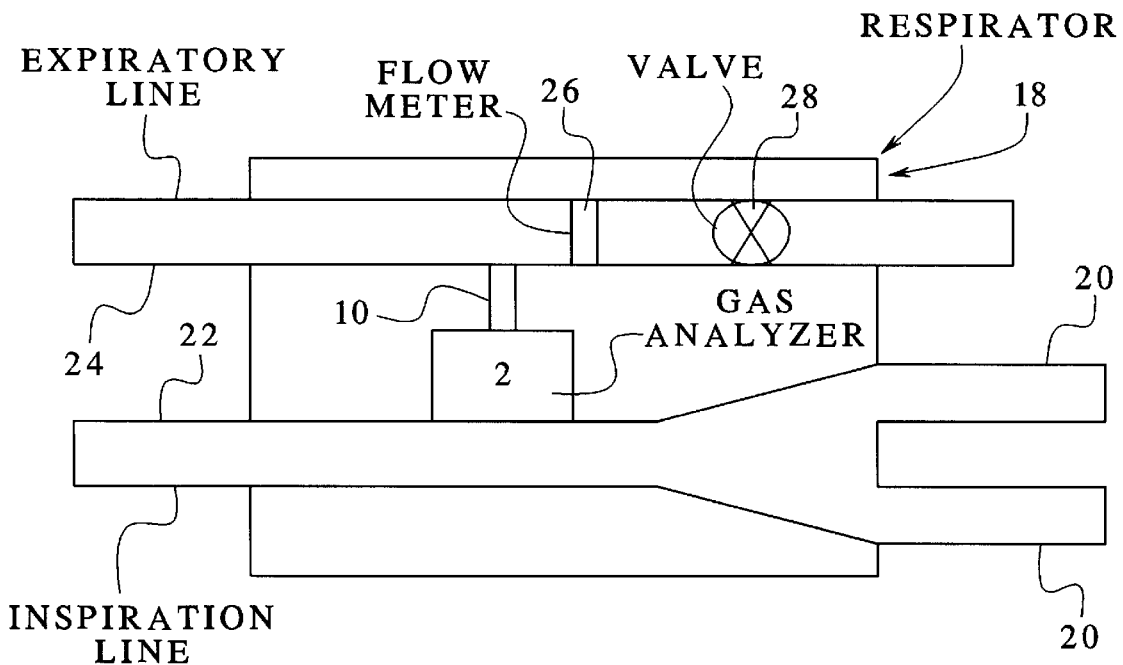

GAS ANALYZER

BACKGROUND OF THE INVENTION

1. Field of the Invention

The present invention is directed to a gas analyzer for determining the concentration of a constituent gas in a gas sample contained in a test chamber, of the type which is sensitive to gas movements inside the test chamber.

2. Description of the Prior Art

A number of different kinds of gas analyzers are available for determining the concentration of a constituent gas in a gas sample, e.g. optical, electrochemical and paramagnetic gas analyzers. The different analyzers have different advantages and disadvantages, depending on the physical principle they employ.

Thus, paramagnetic analyzers have the disadvantage of being sensitive to gas movements inside the test chamber. This means that the analyzer must be located at a distance from the gas line, when measurements are to be made of flowing gas, e.g. as in respirators, and a gas sample must be extracted through a test line with a pump. Therefore every sampling and analysis is encumbered by a time delay.

On the other hand, paramagnetic analyzers have the advantage of not affecting the gas being analyzed. Their performance is also superior, and they are more economical.

It would therefore be advantageous if analyses with paramagnetic analyzers, and other analyzers sensitive to gas movement, could be performed closer to the flow of gas from which the gas sample is to be taken.

SUMMARY OF THE INVENTION

An object of the present invention is to provide a gas analyzer that resolves the aforementioned problems.

Another object is to provide a gas analyzer suitable for use with respirators.

The above objects are achieved in accordance with the principles of the present invention in a gas analyzer, and in a respirator employing a gas analyzer, wherein the gas analyzer has a test chamber for a test sample, an inlet for receiving the gas sample and a gas sensor for determining the concentration of a constituent gas in the gas sample, the gas sensor being sensitive to gas movements, wherein the inlet is directly connectible to an inspiration line of the respirator, and the gas analyzer further including a shield disposed so as to cover the inlet, so that the gas sample in the test chamber stays relatively still during analysis thereof employing the gas sensor, regardless of the flow of gas in the inspiration line.

Through the use of a shield, the gas sample in the test chamber can be kept still, even though the test chamber is directly connected to the flowing gas in the inspiration line. A porous wall, permeable to gas, is sufficient to produce sufficiently still gas, but a valve providing complete shielding is also possible.

Since the gas analyzer is adapted be connected to the flowing gas in such a way, a new gas sample can be taken by utilization of the flow and/or pressure of the flowing gas in the inspiration line. The test chamber's outlet can be connected to the expiratory line. When a valve is used, the gas can be allowed to flow alternately through or remain still inside the test chamber.

DESCRIPTION OF THE DRAWINGS

FIG. 1 shows one embodiment of the gas analyzer according to the invention.

FIG. 2 shows the gas analyzer of FIG. 1 incorporated in a respirator.

DESCRIPTION OF THE PREFERRED EMBODIMENTS

FIG. 1 shows a gas analyzer 2, according to the invention, connected to a gas line 4. A gas, from which a gas sample is extracted for analysis of its concentration of a constituent gas, flow through the line.

The gas analyzer 2 has an inlet 6, a test chamber 8 and an outlet 10. A porous wall 12, permeable to gas, is arranged in the inlet 6 to reduce or prevent gas movement, caused by the gas flowing in the gas line 4, inside the test chamber 8.

A valve 14 for retaining the gas sample inside the test chamber 8 is arranged at the outlet 10. After gas analysis the valve 14 is opened to discharge the gas sample through the outlet 10 while a new gas sample is admitted through the inlet 6 at the same time.

A sensor 16 for the gas analysis is symbolically designated in the gas analyzer 2. The sensor 16 can be a paramagnetic sensor or some other sensor sensitive to gas movement inside the test chamber 8.

FIG. 2 shows an application for the gas analyzer 2 in a respirator 18. The respirator 18 has a gas connector 20 for admitting the gases that compose the breathing gas for a patient. The gases are mixed and carried to the patient through an inspiration line 22. The gas is subsequently carried from the patient through an expiratory line 24, which can contain a flow meter 26 and a valve 28, to atmosphere or an evacuation unit. Respirators of this kind are well known and do not require detailed description in this context.

The oxygen content of the breathing gas is important in respirator care, and the gas analyzer 2 is directly connected to the inspiration line 22 to extract a sample from it in order to measure that content. The extraction can be passive, based on pressure difference between the inlet 6 and the outlet 10. After the analysis, gas samples are sent to the expiratory line 24. The purpose of this is to avoid influencing volume determinations in the respirator 18. When the test chamber 8 has a small measurement volume, e.g. 2 $cm^3$, the gas can be sent directly to atmosphere, or part of the expiratory line 24 after the flow meter 26 or after the valve 28, without any significant impact on volume determinations. The outlet 10 alternatively can be connected directly to atmosphere. Pressure gradients in the system during different phases of the respiratory cycle can be utilized to make gas samples flow from the inspiration line 22 in the gas analyzer 2 and then (after analysis) from the gas analyzer 2 to the expiratory line 24.

Alternative embodiments are possible. For example, the wall 12 can be replaced with a valve or a pump, preferably a pneumatic sponge valve, a micro-mechanical valve or a pump. A porous wall, permeable to gas, can be arranged at the outlet. A pump, preferably a micro-mechanical pump, can be arranged at the outlet to pump gas samples out of the test chamber.

The most salient feature of the invention is the provision of movement-sensitive sensors in the gas analyzer. With a means to shield the gas sample in the test chamber from the influence of flowing gas in the inspiration line, the initially-described disadvantage normally associated with sensors of this type is minimized or avoided, because the gas analyzer can be located as close as possible to the flowing gas.

Although modifications and changes may be suggested by those skilled in the art, it is the intention of the inventor to embody within the patent warranted hereon all changes and modifications as reasonably and properly come within the scope of his contribution to the art.

I claim as my invention:

1. A gas analyzer for use in a respirator having an inspiration line with a flow of gas in said inspiration line, said gas analyzer comprising:

a test chamber at a test chamber pressure;

an inlet directly connectible to said inspiration line for admitting a gas sample from said inspiration line into said test chamber;

a gas sensor disposed in said test chamber for analyzing said gas sample for determining a concentration of a constituent gas in said gas sample, said gas sensor being sensitive to gas movements;

shielding means disposed for covering said inlet after said gas sample is admitted into said test chamber for maintaining said gas sample in said test chamber substantially still during analysis of said gas sample by said gas sensor, independently of the flow of said gas in said inspiration line; and an outlet communicating with said test chamber and communicating with an environment at a pressure which is lower than said test chamber pressure, for passively discharging said gas sample after said gas sample is analyzed by said gas sensor.

2. A gas analyzer as claimed in claim 1 further comprising a valve disposed at said outlet causing a new gas sample to be admitted into said test chamber through said inlet when said valve is opened and the gas sample analyzed by said gas sensor is passively discharged.

3. A gas analyzer as claimed in claim 1 wherein said respirator has an expiratory line, and wherein said outlet is connectible to said expiratory line.

4. A gas analyzer as claimed in claim 1 wherein said gas analyzer comprises means for passively changing said gas sample in said test chamber once for every respiratory cycle of a patient connected to said respirator.

5. A gas analyzer as claimed in claim 1 wherein said shielding means comprises a porous, gas permeable wall.

6. A gas analyzer as claimed in claim 1 wherein said gas sensor comprises a paramagnetic gas sensor.

7. A gas analyzer as claimed in claim 1 wherein said outlet is directly connected to atmosphere.

8. A gas analyzer as claimed in claim 1 further comprising a valve disposed at said inlet causing a new gas sample to be admitted into said test chamber through said inlet when said valve is opened and the gas sample analyzed by said gas sensor is passively discharged.

9. A gas analyzer as claimed in claim 1 further comprising a porous, gas permeable wall covering said outlet.

10. A gas analyzer as claimed in claim 9 wherein said shielding means comprises a further porous, gas permeable wall covering said inlet.

* * * * *